US006333992B1

(12) United States Patent
Yamamura et al.

(10) Patent No.: US 6,333,992 B1
(45) Date of Patent: Dec. 25, 2001

(54) DEFECT JUDGEMENT PROCESSING METHOD AND APPARATUS

(75) Inventors: Hisae Yamamura, Yokohama; Yukio Matsuyama, Tochigi-ken; Toshifumi Honda, Funabashi, all of (JP); Ludwig Listl, Munich (DE)

(73) Assignees: Hitachi, Ltd., Tokyo (JP); Siemens Aktiengesellschaft, Munich (DE)

( * ) Notice: Subject to any disclaimer, the term of this patent is extended or adjusted under 35 U.S.C. 154(b) by 0 days.

(21) Appl. No.: 08/967,015

(22) Filed: Nov. 10, 1997

(30) Foreign Application Priority Data

Nov. 11, 1996 (JP) .................................................. 8-298713

(51) Int. Cl.[7] .................................................. G06K 9/00
(52) U.S. Cl. .......................................... 382/149; 348/126
(58) Field of Search ..................................... 382/141, 144, 382/145, 147, 149, 205; 348/126; 356/394

(56) References Cited

U.S. PATENT DOCUMENTS

| 4,448,532 | * | 5/1984 | Joseph et al. ........................ 356/394 |
| 4,953,100 | | 8/1990 | Yotsuya . |
| 5,058,178 | | 10/1991 | Ray . |
| 5,761,337 | | 6/1998 | Nishimura et al. . |
| 5,822,449 | * | 10/1998 | Kobayashi et al. .................. 382/141 |

FOREIGN PATENT DOCUMENTS

| 0 277 502 A1 | 8/1988 | (EP) . |
| 0 687 901 A1 | 12/1995 | (EP) . |
| 0 718 623 A2 | 6/1996 | (EP) . |

* cited by examiner

*Primary Examiner*—Bhavesh Mehta
(74) *Attorney, Agent, or Firm*—Antonelli, Terry, Stout & Kraus, LLP

(57) ABSTRACT

A defect judgement processing method and apparatus which can optimize image processing and defect judgement parameters for a detection image cut out by each inspection window to avoid erroneous judgement and defect missing and to realize reliable defect judgement. An image data generator cuts out ranges indicated by a plurality of predesignated inspection windows from a detected image and stores them in a memory, a window data generator generates window data having inspection conditions attached thereto with respect to the plurality of inspection windows and stores them in the memory, a feature extractor reads out detection images of the ranges indicated by the inspection windows from the memory and extracts a structural feature parameter therefrom on the basis of an image processing parameter conforming to the inspection condition obtained by the window data, and a defect judger performs its defect judging operation over the extracted structural feature parameter on the basis of a defect judgement parameter conforming to the inspection condition.

28 Claims, 9 Drawing Sheets

FIG. 4

| index | IMAGE PROCESSING RANGE | INSPECTION CONTENTS | PART NUMBER | PIN NUMBER | LEAD DIRECTION | PART TYPE | LEAD ADDRESS | DATA SIZE |
|---|---|---|---|---|---|---|---|---|
| 0 | (xs(0), ys(0)) - (xe(0), ye(0)) | SOLDERED | 0 | 1 | LEFT | 1.27mm SOP | addr(0) | size(0) |
| 1 | (xs(1), ys(1)) - (xe(1), ye(1)) | BRIDGE | 0 | 1 | LEFT | 1.27mm SOP | addr(1) | size(1) |

13 INSPECTION WINDOW DATA

14 WINDOW DATA

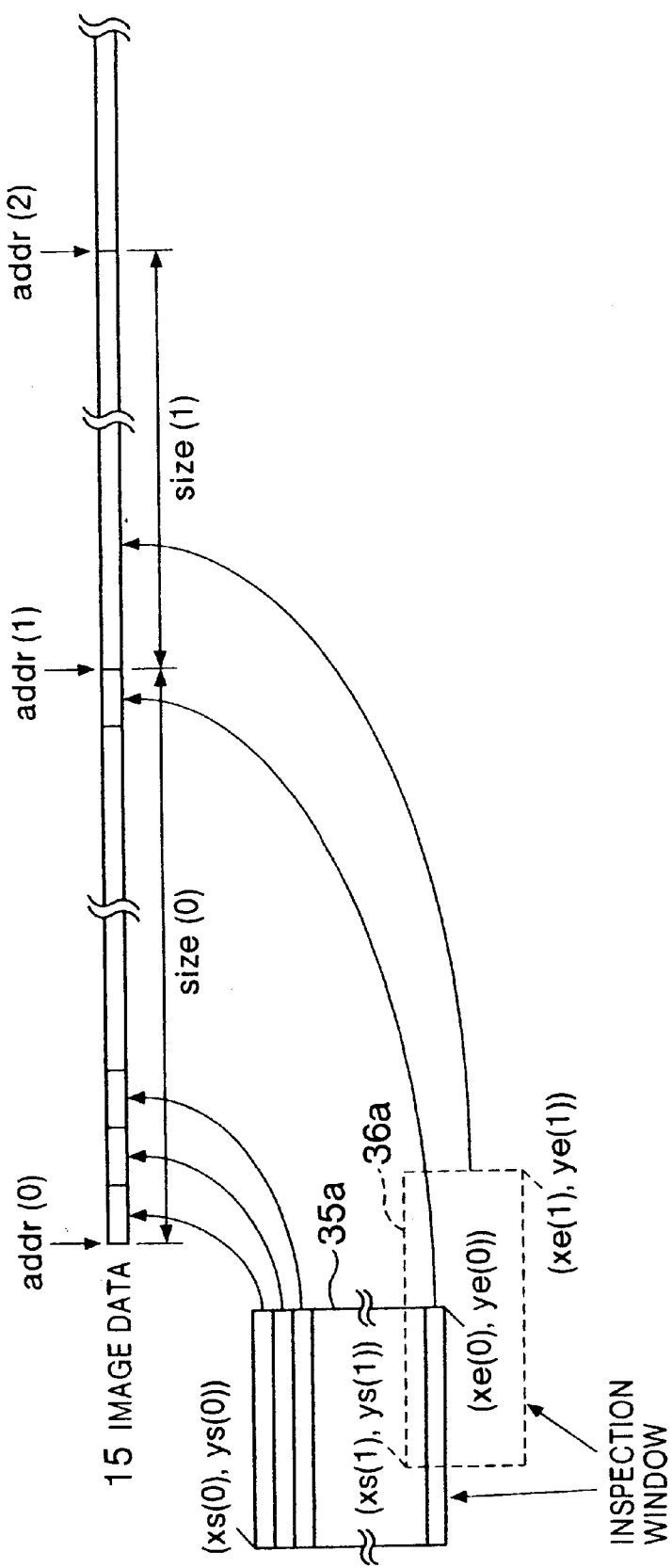

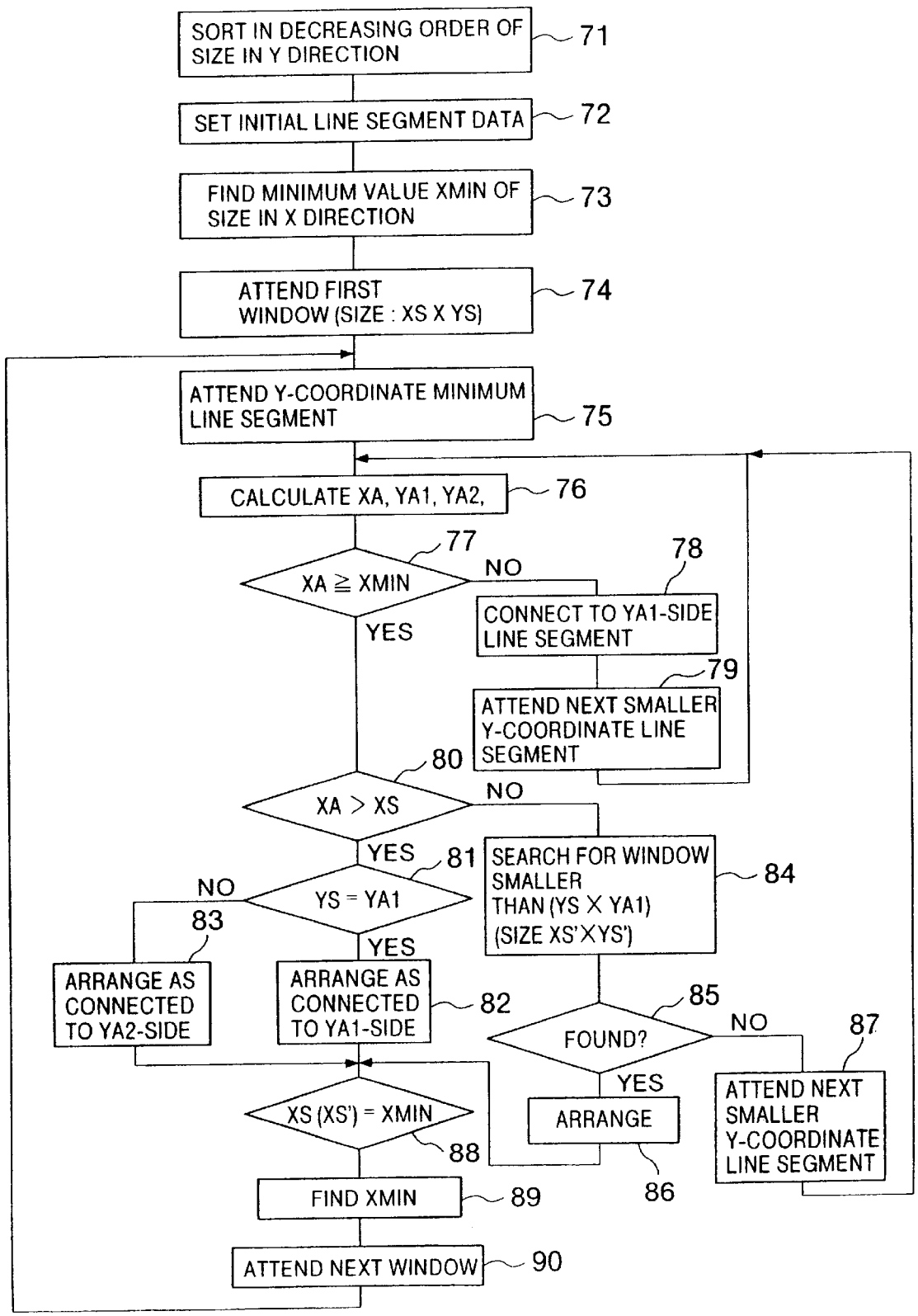

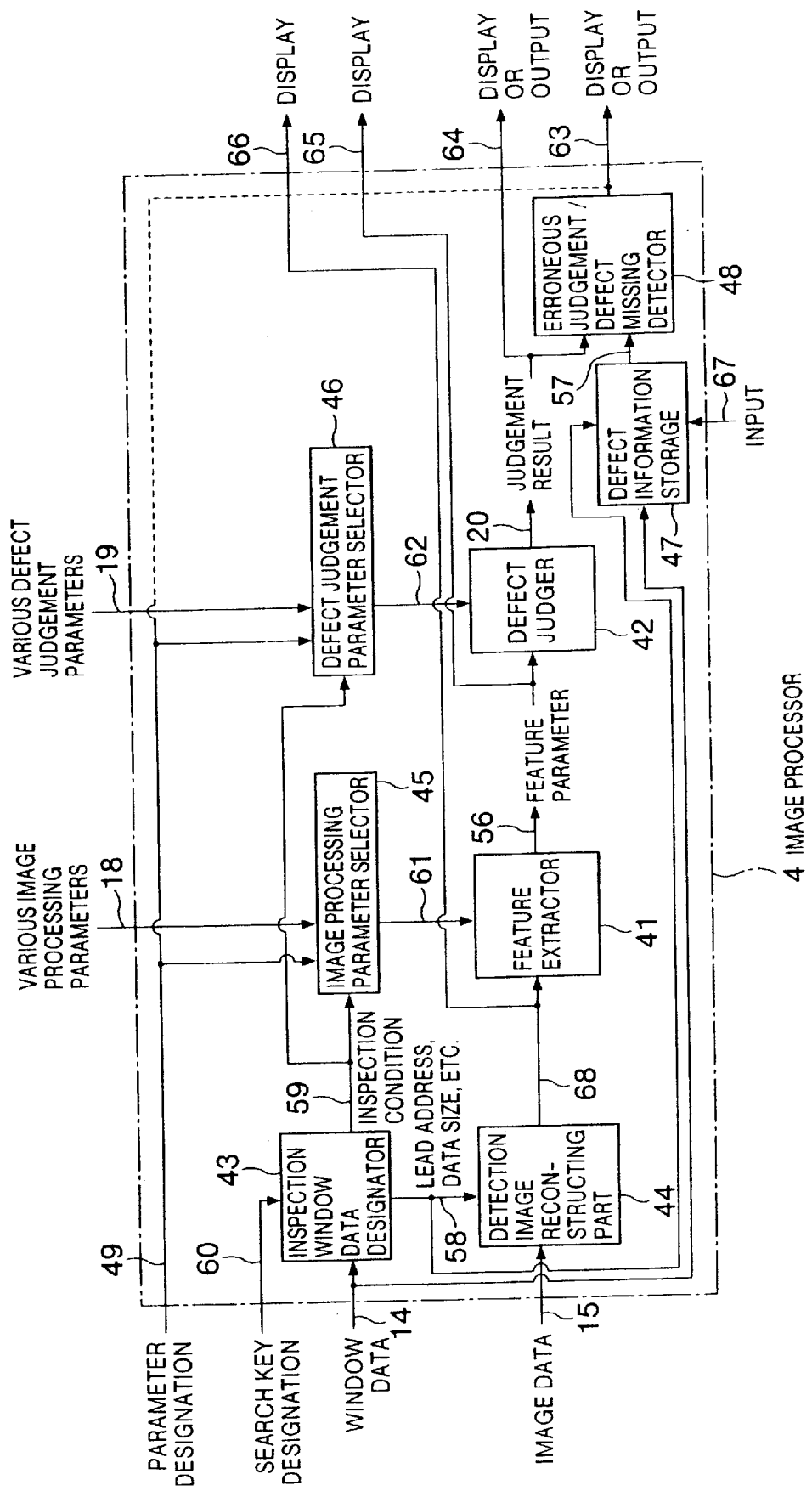

DEFECT JUDGEMENT PROCESSING METHOD AND APPARATUS

BACKGROUND OF THE INVENTION

The present invention relates to a defect judgement processing method and apparatus which selectively collects necessary image data from a detected image and applies image processing operation to the collected image data to perform defect judgement.

In conventional visual inspections, there has been known a technique by which positional information on inspection points of such an object to be inspected as, e.g., a parts-mounted substrate are previously registered as inspection window data so that an image including the inspection points is detected to perform defect judgement on the basis of image processing of ranges indicated by the inspection window data.

The aforementioned prior art, which requires a lot of parameters for use in the image processing and defect judgement and further requires parameters corresponding to various types of parts to be separately set, has had a problem that it takes a lot of time to optimize the parameters.

SUMMARY OF THE INVENTION

It is an object of the present invention to provide a defect judgement processing method and apparatus which can optimize image processing parameters and defect judgement parameters of the detection image cut out by each inspection window to eliminate erroneous judgement for a good product or defect missing and to thereby realize reliable defect judgement.

An other object of the present invention is to provide a defect judgement processing method and apparatus which, when performing reliable defect judgement of a detection image cut out by each inspection window, can optimize, in simulation, image processing parameters and defect judgement parameters to avoid judgement of a good product as wrong or defect missing.

In accordance with the present invention, the above objects are attained by providing a defect judgement processing method which is characterized by comprising the steps of detecting by image detection means an image of an object to be inspected, cutting out by image data generator means ranges indicated by a plurality of predesignated inspection windows from the detected image and storing the ranges in memory means, generating by window data generator means window data having an inspection condition attached thereto for each of said plurality of inspection windows and storing the window data in said memory means, reading out by a feature extractor the detection image of the range indicated by each inspection window from said memory means, reading out the window data corresponding to the respective inspection windows stored in said memory means and extracting a structural feature parameter therefrom on the basis of an image processing parameter conforming to the inspection condition obtained by each window data, and performing by a defect judger its defect judging operation over the extracted structural feature parameter on the basis of a defect judgement parameter conforming to said inspection condition.

Further, in accordance with the present invention, there is provided a defect judgement processing method which is characterized by comprising the steps of detecting by image detection means an image of an object to be inspected, cutting out by image data generator means ranges indicated by a plurality of predesignated inspection windows from the detected image and storing the ranges in memory means, generating by window data generator means window data having an inspection condition attached thereto for each of said plurality of inspection windows and storing the window data in said memory means, reading out by a feature extractor the window data corresponding to the respective inspection windows stored in said memory means, selecting an image processing parameter conforming to the inspection condition obtained by each window data and further extracting a structural feature parameter from the detection image of the range indicated by each inspection window read out from said memory means on the basis of said selected image processing parameter, and selecting by a defect judger the structural feature parameter conforming to said inspection condition and performing its defect judging operation over the extracted structural feature parameter on the basis of said selected defect judgement parameter.

In accordance with the present invention, there is provided a defect judgement processing method which is characterized by comprising the steps of detecting by image detection means an image of an object to be inspected, cutting out by image data generator means ranges indicated by a plurality of predesignated inspection windows from the detected image and storing the ranges in memory means, generating by window data generator means window data having an inspection condition attached thereto for each of said plurality of inspection windows and storing the window data in said memory means, reading out a feature extractor the detection image of the range indicated by each inspection window from said memory means, reading out the window data corresponding to the respective inspection windows stored in said memory means and extracting a structural feature parameter therefrom on the basis of an image processing parameter conforming to the inspection condition obtained by each window data, and performing by a defect judger its defect judging operation over the extracted structural feature parameter on the basis of a defect judgement parameter conforming to said inspection condition and comparing its defect judgement with defect information previously stored as associated with said each inspection window to detect erroneous judgement or defect missing.

In accordance with the present invention, there is provided a defect judgement processing method which is characterized by comprising the steps of detecting by image detection means an image of an object to be inspected, cutting out by image data generator means ranges indicated by a plurality of predesignated inspection windows from the detected image and storing the ranges in memory means, generating by window data generator means window data having an inspection condition attached thereto for each of said plurality of inspection windows and storing the window data in said memory means, reading out by a feature extractor the detection image of the range indicated by each inspection window from said memory means, reading out the window data corresponding to the respective inspection windows stored in said memory means and extracting a structural feature parameter therefrom on the basis of an image processing parameter selected according to the inspection condition obtained by each window data, and performing by a defect judger its defect judging operation over the extracted structural feature parameter on the basis of a defect judgement parameter selected according to said inspection condition, comparing its defect judgement with defect information previously stored as associated with said each inspection window to detect erroneous judgement or defect missing, and optimizing said selected image processing parameter or defect judgement parameter according to the detected erroneous judgement or defect missing.

In accordance with the present invention, there is provided a defect judgement processing method which is characterized by comprising the steps of detecting by image detection means an image of an object to be inspected, cutting out by image data generator means ranges indicated by a plurality of predesignated inspection windows from the detected image and storing the ranges in memory means, generating by window data generator means window data having an inspection condition attached thereto for each of said plurality of inspection windows and storing the window data in said memory means, reading out by a feature extractor the detection image of the range indicated by each inspection window from said memory means, reading out the window data corresponding to the respective inspection windows stored in said memory means and extracting a structural feature parameter therefrom on the basis of an image processing parameter conforming to the inspection condition obtained by each window data, and performing by a defect judger its defect judging operation over the extracted structural feature parameter on the basis of a defect judgement parameter conforming to said inspection condition and comparing its defect judgement with defect information previously stored as associated with said each inspection window to detect erroneous judgement or defect missing and to display it on display means.

In accordance with the present invention, there is provided a defect judgement processing method which is characterized by comprising the steps of detecting by image detection means an image of an object to be inspected, cutting out by image data generator means ranges indicated by a plurality of predesignated inspection windows from the detected image and storing the ranges in memory means, generating by window data generator means window data having an inspection condition attached thereto for each of said plurality of inspection windows and storing the window data in said memory means, reading out by a feature extractor the detection image of the range indicated by each inspection window from said memory means, reading out the window data corresponding to the respective inspection windows stored in said memory means and extracting a structural feature parameter therefrom on the basis of an image processing parameter conforming to the inspection condition obtained by each window data, and performing by a defect judger its defect judging operation over the extracted structural feature parameter on the basis of a defect judgement parameter conforming to said inspection condition, displaying its defect judgement on display means, and comparing its defect judgement with defect information previously stored as associated with said each inspection window to detect erroneous judgement or defect missing and to display it on the display means.

In accordance with the present invention, there is provided a defect judgement processing method which is characterized by comprising the steps of detecting by image detection means an image of an object to be inspected, cutting out by image data generator means ranges indicated by a plurality of predesignated inspection windows from the detected image and storing the ranges in memory means, generating by window data generator means window data having an inspection condition attached thereto for each of said plurality of inspection windows and storing the window data in said memory means, reading out by a feature extractor the detection image of the range indicated by each inspection window from said memory means, reading out the window data corresponding to the respective inspection windows stored in said memory means and extracting a structural feature parameter therefrom on the basis of an image processing parameter conforming to the inspection condition obtained by each window data, and performing by a defect judger its defect judging operation over the extracted structural feature parameter on the basis of a defect judgement parameter conforming to said inspection condition, displaying said extracted structural feature parameter on display means, and comparing its defect judgement with defect information previously stored as associated with said each inspection window to detect erroneous judgement or defect missing and to display it on the display means.

In accordance with the present invention, there is provided a defect judgement processing method for applying an image processing operation to perform defect judgement, characterized by comprising the steps of specifying as a search key part of items of inspection window data including data for specifying an image processing range and an inspection condition, selecting the inspection window data on the basis of the specified search key, and cutting out only the data of a detection image of the range indicated by the selected inspection window data to collect image data and store it.

In accordance with the present invention, there is provided a defect judgement processing apparatus which is characterized by comprising image detection means for detecting an image of an object to be inspected, memory means, image data generator means for cutting out ranges indicated by a plurality of predesignated inspection windows from the detected image and for storing the ranges in said memory means, window data generator means for generating window data having an inspection condition attached thereto for each of said plurality of inspection windows and for storing the window data in said memory means, feature extraction means for reading out the detection image of the range indicated by each inspection window from said memory means, for reading out the window data corresponding to the respective inspection windows stored in said memory means and for extracting a structural feature parameter therefrom on the basis of an image processing parameter conforming to the inspection condition obtained by each window data, and defect judgement means for performing its defect judging operation over the extracted structural feature parameter on the basis of a defect judgement parameter conforming to said inspection condition.

In accordance with the present invention, there is provided a defect judgement processing apparatus which is characterized by image detection means for detecting an image of an object to be inspected, memory means, image data generator means for cutting out ranges indicated by a plurality of predesignated inspection windows from the detected image and for storing the ranges in said memory means, window data generator means for generating window data having an inspection condition attached thereto for each of said plurality of inspection windows and for storing the window data in said memory means. feature extraction means for reading out the detection image of the range indicated by each inspection window from said memory means, for reading out the window data corresponding to the respective inspection windows stored in said memory means and for extracting a structural feature parameter therefrom on the basis of an image processing parameter conforming to the inspection condition obtained by each window data, defect judgement means for performing its defect judging operation over the extracted structural feature parameter on the basis of a defect judgement parameter conforming to said inspection condition, and detection means for comparing a defect judgement result obtained by said defect judgement means with defect information previously stored as associated with said each inspection window to detect erroneous judgement or defect missing.

In accordance with the present invention, there is provided an image data collecting method which comprises the steps of, when the image processing is applied to perform the defect judgement, generating and storing window data for specifying the range associated with each inspection window, and cutting out only the image data of the range indicated by each inspection window data from the detection image on the basis of the stored window data.

In accordance with the present invention, there is provided an image data collecting method which comprises the steps of, when the image processing is applied to perform the defect judgement, specifying as a search key part of items of inspection window data including data for specifying the image processing range and inspection condition, selecting the inspection window data on the basis of the specified search key, and cutting out and storing only the data of the detection image of the range indicated by the selected inspection window data.

In accordance with the present invention, there is provided an inspection apparatus which has an image detection optical system for detecting an image of an object to be inspected, a movable stage for holding the inspection object or said image detection optical system, and an image processor for performing defect judgement through the image processing of the range indicated by a plurality of prespecified inspection window data; and which is characterized by comprising an image data generator for cutting out only data of the range indicated by each inspection window data from the detection image, a window data generator for generating window data for specifying the range associated with each inspection window with respect to said image data, and a memory device for storing said window data and said image data.

In the present invention, said image processor is featured by performing the defect judgement by applying the image processing of the range indicated by said window data with use of the inspection parameters preset for said image data. In the present invention, further, said image data generator is featured in that generation of the image data is carried out by sequentially copying the data of the detection image of the ranges indicated by the respective inspection window data to a one-dimensional array. In the present invention, furthermore, said window data generator is featured in that generation of the window data is carried out by attaching a lead address and data size of the associated image data to each inspection window data. In the invention, said window data generator is featured in that generation of the window data in said window data generator is carried out by arranging the respective windows having the same size and attribute as the respective inspection windows in such a manner that there is no overlap between the inspection windows and all the windows and that, when being included within a rectangular region having the same width as the image, the size of said rectangular region becomes minimum. Said image data generator is featured in that generation of the image data in said image data generator is carried out, in an image detection mode, by copying the data of the detection image of the range indicated by each inspection window data to a position indicated by the associated window data.

In the present invention, there is provided an inspection apparatus which is characterized by comprising a window data generator for generating window data by arranging the respective windows having the same size and attribute as the respective inspection windows in such a manner that there is no overlap between the windows and all the windows and that, when being included within a rectangular region having the same width as the image, the size of said rectangular region becomes minimum; an image data generator for generating the image data by copying the data of the detection image of the range indicated by each inspection window data to a position indicated by the associated window data; and an image processor for performing its defect judging operation by applying to said image data the image processing of the range indicated by said window data.

As has been explained above, in accordance with the present invention, since only the data of the range indicated by each inspection window data is cut out from the detection image, the data capacity can be remarkably reduced when compared with that of the detection image without deteriorating information necessary for the defect judgement and a write time to the image memory device can also be made short. Further, since the window data for specifying the range of the image processing associated with each inspection window is generated, simulation of defect judgement based on the image processing equivalent to the inspection can be easily implemented by inputting said image data and said window data. That is, parameter optimization can be easily realized by generating simulation data to many inspection points and repeating the defect judging simulation while changing the parameter.

In accordance with the present invention, with respect to the detection image cut out by each inspection window, the image processing parameter and defect judgement parameter are optimized so that reliable defect judgement can be realized without any erroneous judgement or defect missing.

In accordance with the present invention, when the detection image cut out by each inspection window is subjected to the defect judgement with a high reliability, there can be realized such simulation that optimizes the image processing parameter and defect judgement parameter to avoid erroneous judgement and defect missing.

BRIEF DESCRIPTION OF THE DRAWINGS

FIG. 4 shows an example of inspection window data and widow data.

FIG. 5 is a diagram for explaining how to generate simulating image data.

FIG. 7 shows a flowchart for arranging and generating the simulating windows.

FIG. 9 is a functional block diagram of a detailed arrangement of an image processor in FIG. 9.

DESCRIPTION OF THE PREFERRED EMBODIMENTS

An embodiment of the present invention will be explained with reference to the drawings.

Figure 1:
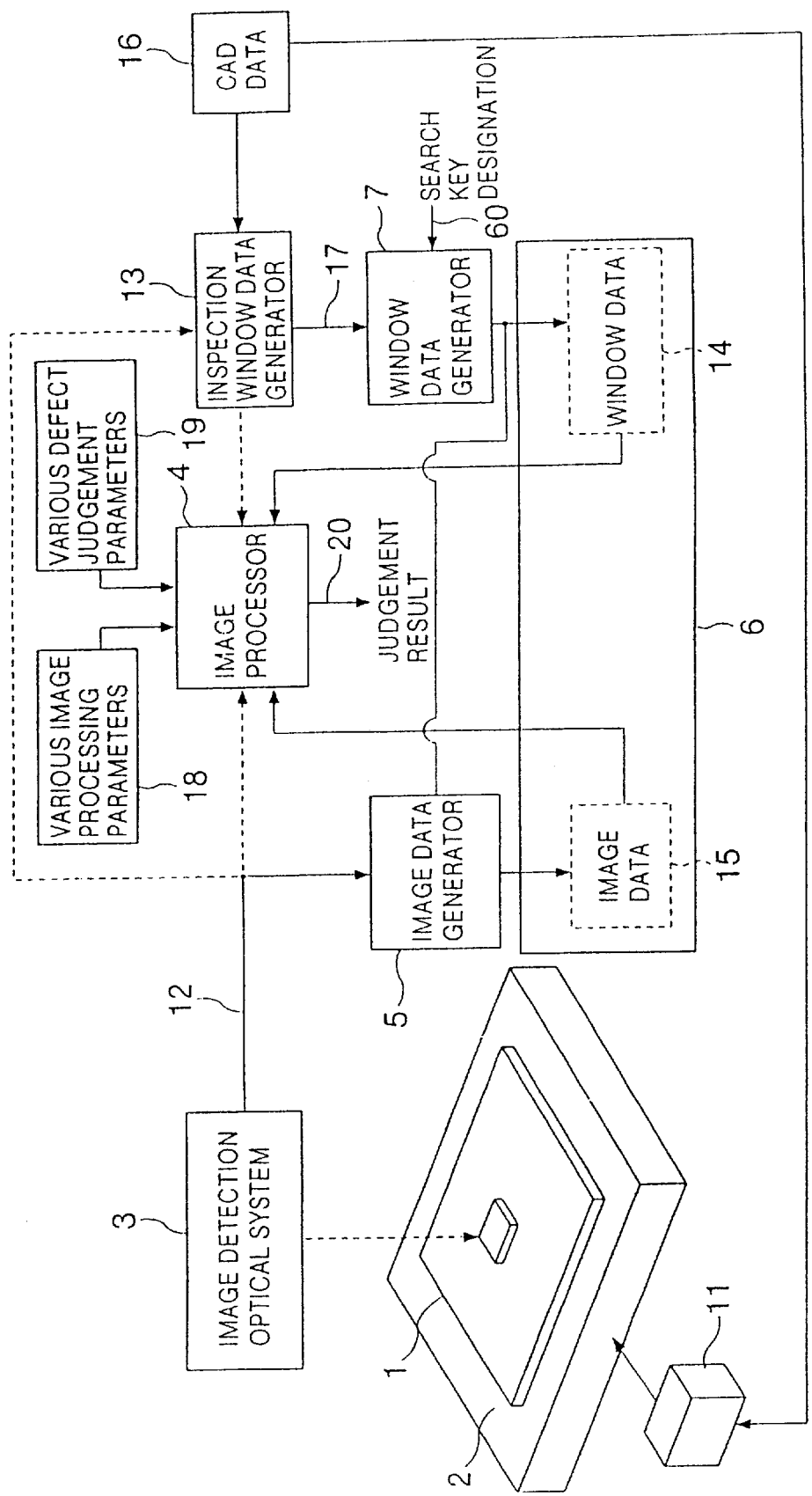
FIG. 1 shows a schematic arrangement of an inspection apparatus in accordance with an embodiment of the present invention.
Figure 2:
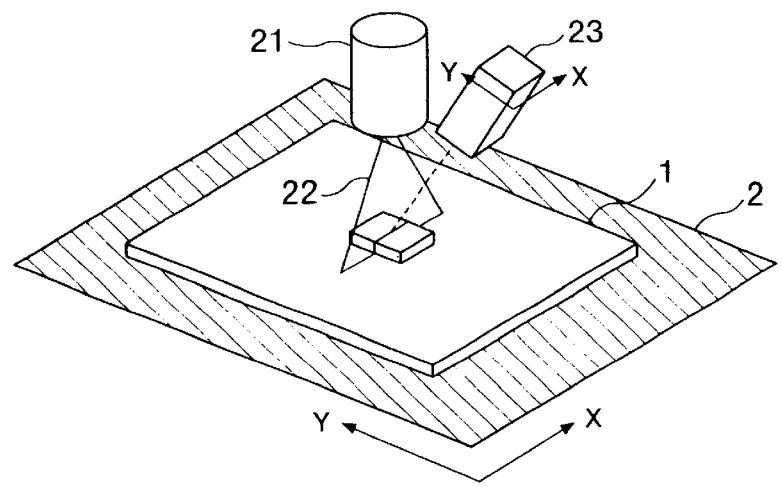
FIG. 2 shows a perspective view of a detailed example of an image detection optical system in FIG. 1.

FIG. 1 is a schematic arrangement of a visual inspection apparatus in accordance with an embodiment of the present invention.

A wired structure (parts-mounted board) 1 to be inspected is held on a stage 2 to be movable in X and Y directions. The stage 2 is controlled by a controller 11 on the basis of predesignated stage control data. An image detection optical system 3 detects a detection image 12 as a gray or distance image including points to be inspected. Reference numeral 4 denotes an image processor which, in a normal inspection mode, receives the detection image 12 from the image detection optical system 3 and performs defect judgement through image processing of an image processing range indicated by predesignated inspection window data 13. Meanwhile, an image data generator 5, which mainly comprises an image signal cut-out circuit, accepts the detection image 12 from the image detection optical system 3, cuts out image data of the image processing range specified by the inspection window concurrently with the defect judgement, applies to the cut-out image data a lead address addr(i) and data size size(i) given by the window data 14 to convert the data to such a one-dimensional array as shown in FIG. 5 and to generate simulating image data 15, and stores the simulating data in a memory device 6 formed as a hard disk, memory card or semiconductor memory. The inspection window data generator 13 generates inspection window data 17 including the image processing range, inspection contents, part number (electronic part number), pin number, lead direction and part type (electronic part type) as shown in FIG. 4 on the basis of CAD data 16 of an inspection object received from an upper-level system. A window data generator 7, prior to the image detection of the image detection optical system 3 or simultaneously therewith, generates such simulating window data 14 having the lead address addr(i) and data size size(i) attached thereto as shown in FIG. 4 on the basis of the inspection window data 17 of FIG. 4 received from the inspection window data generator 13, and stores it in the memory device 6. The inspection window data generator 13 or window data generator 7 comprises, as major elements, a CPU, a ROM for previously storing therein an inspection window data generating program and a window data generating program, a RAM for storing therein the inspection window data or window data generated by the CPU, a display means for displaying the data, an input means such as an input keyboard, and an interface (I/F) for interconnection with the above memory device 6 or with the above system providing the CAD data through buses. The memory device 6, which comprises a hard disk, memory card or semiconductor memory, acts to store therein the simulating window data 14 generated by the window data generator 7 and the simulating image data generated by the image data generator 5. In a simulation mode, the image processor 4 specifies the lead address and data size within the simulating window data 14 to read out the stored image data 15 from the memory device 6 and to restore it to a detection image 68, extracts from the restored detection image 68 such a structural feature parameter 56 as a two- or three-dimensional shape or physical property on the basis of an image processing parameter 61 selected from various image processing parameters 18 under an inspection condition 59, performs its defect judging operation over the structural feature parameter 56 on the basis of a defect judgement parameter 62 selected from various defect judgement parameters 19 under the inspection condition 59, and then outputs its judgement result 20, (which details are shown in FIG. 9). That is, the image processor 4 reads out the simulating image data 15 from the memory device 6 and applies image processing operation with respect to the specified image processing range on the basis of the simulating window data 14 to perform defect judgement. The image processor 4 also comprises, as main component elements, a CPU; a ROM for storing therein a restoration program, a structural feature parameter extraction program, a defect judgement program, etc.; a memory for storing therein the detection image restored by the CPU; a RAM for storing therein the structural feature parameter extracted by the CPU and the defect judgement result; a display means; an input means such as an input keyboard; and an interface (I/F) for interconnection with the above memory device 6 or with the above window data generator 7 through bases. In this connection, the image processor 4 may be combined with the inspection window data generator 13 and window data generator 7 into a single unit.

Although the above embodiment has been explained in connection with the case where the embodiment comprises the separated inspection window data generator 13 and window data generator 7, the inspection window data generator 13 and window data generator 7 may obviously be combined into a single window data generator.

Further, the above explanation has been made in connection with the case where the wired structure (parts-mounted board) 1 to be inspected is held (mounted) on the stage 2 movable in the X and Y directions in the foregoing embodiment, the image detection optical system 3 may obviously be installed on the stage 2 movable in the X and Y directions. In either case, it is preferable that the wired structure (parts-mounted board) 1 to be inspected be held (mounted) on the stage 2 movable in the X and Y directions, because its positioning control can be carried out stably.

Figure 3:
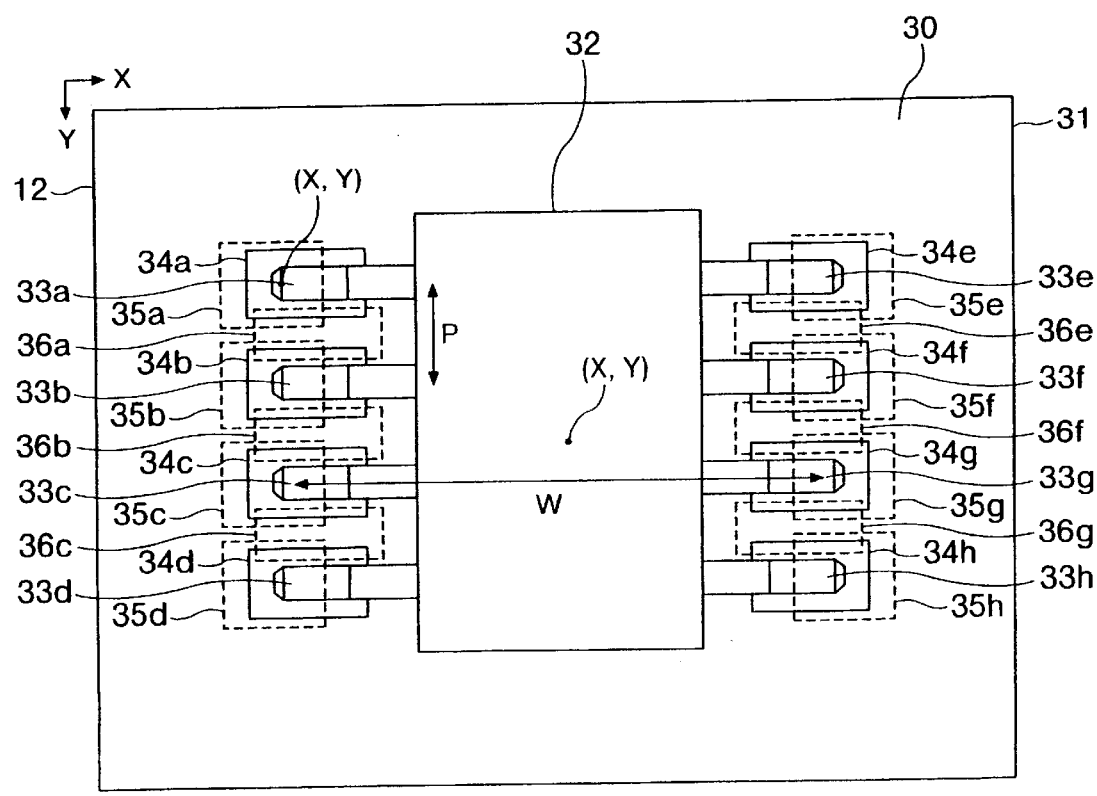
FIG. 3 is a diagram for explaining how to specify inspection windows for a detection image.

Explanation will next be made as to the image detection optical system 3, etc. FIG. 3 shows an example of the image detection optical system 3 for detecting a distance image of an object to be inspected.

The object 1 to be inspected (board to be inspected) is held on the stage 2 movable in the X and Y directions. A slit light projector 21 is positioned so that slit light 22 long in the X direction of the stage 2 illuminates the inspection object 1 from its right above side. A TV camera 23 photographs the inspection object 1 illuminated with the slit light 22 from its oblique direction to obtain a light cut image. In the illustrated example, the TV camera 23 is positioned so that an X axis of an image pickup plane is parallel to the X direction of the stage 2. When a gravity position (central position) of the obtained light cut image in a Y direction is computed with respect to each X coordinate, a height of the inspection object in the X direction Is detected. When the stage 2 is scanned in the Y direction, a distance image indicative of a stereoscopic shape of the inspection object 1 can be detected. The image detection optical system 3 may be replaced by such a system that the stage is moved to a prespecified position so that the inspection object 1 is illuminated obliquely in the form of ring illumination and photographed by, e.g. a TV camera from its right above side to thereby detect a gray image signal indicative of a stereoscopic shape of the inspection object 1.

Further, when a reflection factor or transmissivity of the light obtained from the inspection object 1 is detected as a gray image signal, physical properties of the inspection object 1 based on a difference in the light reflection factor or transmissivity can be detected as the gray image signal.

Then explanation will be detailed as to the image processor 4, image data generator 5, memory device 6 and window data generator 7.

Shown in FIG. 3 is an example of inspection window data when a wired board structure 30 having an electronic part 32 mounted on a wired board 31 is to be used as the inspection object 1. Reference numeral 12 denotes a detection image as a distance image which is detected by the image detection optical system 3 and which is indicative of a stereoscopic shape (height) of the wired board structure 30 in light and shade. Numeral 32 denotes an electronic part mounted on the wired board 31. Numerals 33a to 33h denote leads of the electronic part 32, and 34a to 34h denote pads on the wired board 31.

Contents of inspection of the wired board structure 30 include, for example, soldered states of tip ends of the leads and the presence or absence of a bridge between the leads. With respect to a window for the above soldered state inspection, image processing ranges 35a to 35h of images centered on each of the tip ends of the leads are specified. With respect to a window for the above bridge inspection, image processing ranges 36a to 36c and 36e to 36g of images between the pads. The specification of the image processing ranges is carried out by the inspection window data generator 13. That is, window sizes are previously determined for, e.g., part types (corresponding to types of electronic parts), so that the inspection window data generator 13 computes positions of the tip ends of the leads on the basis of design information about a mounted position (corresponding to its part number and pin numbers) and mounted direction (corresponding to a lead direction) of the electronic part 32 and also on the basis of data indicative of its part shape with respect to the wired board 31, obtained from the CAD data 16, to position (set) the windows centered on the lead tip end positions (x,y). In the case of FIG. 3, when a width W of the electronic part including the leads, a lead pitch p and the number N of leads provided on its one side are input as electronic part shape data from the CAD data 16; the CPU in the inspection window data generator 13 calculates a tip end position (x,y) of the lead 33a in accordance with expressions (1) and (2) which follow, using the mounted position (X,Y) (which mounted position coordinates are set based on a reference point on the wired board 31 as an origin) of the electronic part inputted from the CAD data 16.

$$x=X-W/2 \qquad (1)$$

$$y=Y-((N-1)\times p/2) \qquad (2)$$

Further, the inspection window data generator 13 may detect an edge of a body of the electronic part 32 through the image processing from the detection image 12, and set an inspection window at a predetermined position on the basis of the shape data of the electronic part inputted from the CAD data 16 with use of the detected body edge as a reference.

The inspection window data, as shown in FIG. 4, include, in addition to the information on the image processing range, information for determining inspection conditions of inspection contents, part type (electronic part type) and lead direction as well as information of part number (electronic part number) and pin number for specifying the window.

Explanation will next be made as to an example of collection of image data in the present invention. That is, the inspection window data 17, which forms a base of the simulating window data 14, include, as shown in FIG. 4, the information indicative of the image processing range, the information for determining the inspection conditions of the inspection contents, part type and lead direction, and the information of the part number and pin number for specifying the window. The inspection window data 17 are generated on the basis of the CAD data 16 of the inspection object obtained from the upper-level system. At this time, with respect to the coordinates of the detection image for which a window is to be set, it is necessary to pay consideration to the imaging magnification of the inspection object (associated with the CAD data). The image processing range can be expressed, for example, by an upper left corner coordinate point (xs(i),ys(i)) of the window and by a lower right corner coordinate point (xe(i),ye(i)). The window data generator 7 copies the inspection window data 17, and attaches thereto the lead address addr(i) and data size size(i) of the image data of each window to prepare the simulating window data 14. The image data generator 5 rearranges the detection image in the image processing range indicated by the inspection window data in the form of a one-directional array of scanning lines to form image data as shown in FIG. 5, and then stores it in the memory device 6. In this connection, the image data generator 5 may cut out the detection image in the image processing range indicated by the inspection window data and then store it in the memory device 6 as it is as shown in FIG. 6(c). In this case, a detection image reconstructing part 44 (to be explained later) in the image processor 4 becomes unnecessary. In this case, the image processor 4 may be arranged, on the basis of window data 58 specified by a inspection window data designator 43, to read out the image data corresponding to the window data 58 from the memory device 6 and to input it to a feature extractor 41 as the detection image 68.

The data size size(i) of image data in each window generated by the window data generator 7 can be calculated in accordance with an expression (3) which follows, since the width of the window is (xe(i)−xs(i)+1) and the number of scanning lines in the window is (ye(i)−ys(i)+1).

$$size(i)=(xe(i)-xs(i)+1)\times(ye(i)-ye(i)+1) \qquad (3)$$

Further, the lead address addr(i) of image data in each window generated by the window data generator 7 can be calculated by an expression (4) which follows.

$$addr(i)=0(i=0) addr(i)=addr(i-1)+size(i-1)(i>0) \qquad (4)$$

Generation of these window data may be carried out before the inspection or simultaneously with the image data generation, i.e., simultaneously with the inspection. It is also possible to designate part of items of the inspection window data as a search key 60 to the window data generator 7, generate the simulating window data 14 in the window data generator 7 with respect to only the inspection window searched by the designated search key 60, and generate the simulating image data 15 in the image data generator 5 on the basis of the simulating window data 14.

Explanation will next be made as to another example of collection of image data in the present invention, which is different from the embodiment of FIG. 5. That is, the window data generator 7, prior to image detection, arranges simulating windows each having the same size and attribute as each inspection window in such a manner that the simulation windows have the same widths as their reconstructed images without overlapping and the size of a rectangular region containing all the windows becomes minimum, and then stores them in the memory device 6. The image data generator 5, in an image detection mode, secures a memory region for the size of the rectangular region and stores (copies) the simulating image data 15 of the detection image of the image processing range indicated by each inspection window in the memory device 6 at a position indicated by the associated window data as shown in FIG. 6C. Through the above operations, the simulating window data 14 having the same size and attribute as each inspection window as well as the simulating image data 15 having the same width as the detection image are generated and stored in the memory device 6.

Explanation will then be made as to how to arrange such simulating windows as mentioned above.

Figure 6A:
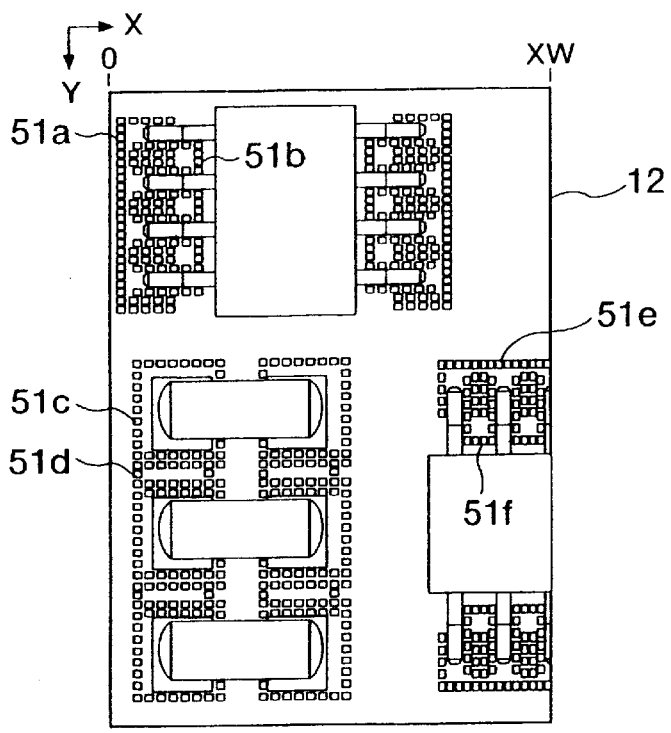
FIGS. 6A–6C show diagrams showing a positional relationship between the inspection and simulating windows.
Figure 6B:
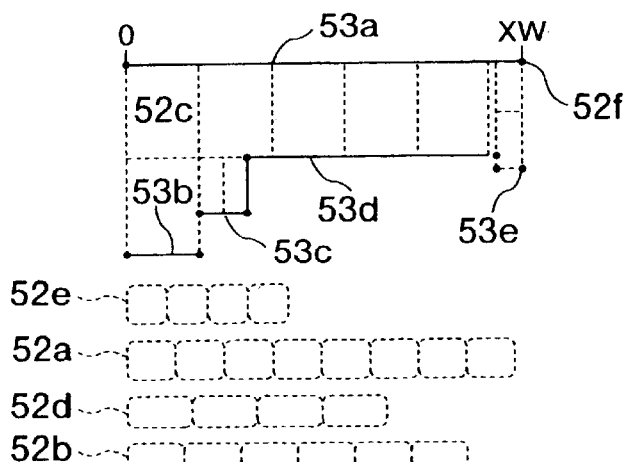
Figure 6C:
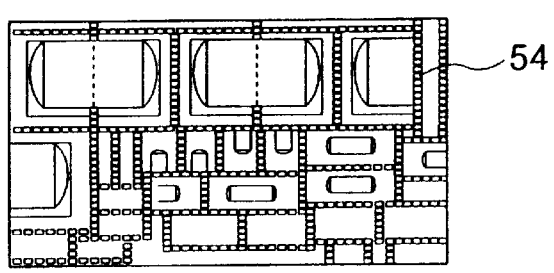

FIG. 6A shows an example of the detection image 12 displayed as overlapped with the inspection windows, FIG. 6B shows an intermediate state of arrangement of the simulating windows, and FIG. 6C shows a completed arrangement of the simulating windows and the simulating image data 15 generated based thereon. In the drawings, reference symbols 51a to 51f denote inspection windows and 52a to 52f denote windows. For the convenience of explanation, continuous line parts 53b to 53e of the already-arranged windows at their lower ends are called line segments, herein. Line segment data indicative of the line segment have x and y coordinate points indicative of its start point and end point. It is assumed in this example that the x axis is directed rightwards and the y axis is downwards.

FIG. 7 is a flowchart for explaining the operation of the window data generator 7.

First, at a step 71, the inspection window data 17 indicated, for example, by 51a to 51f are previously sorted in a decreasing order of size in the y direction. At a step 72, the y coordinate value is set at 0, the x coordinate value of the start point of the line segment is set at 0, and the x coordinate value of the end point thereof is set at a width XW of the detection image, as the initial line segment data 53a, which is illustrated by 53a in FIG. 6B. In a next step 73, a minimum Xmin of the size of the window in the x direction is found. At a next step 74, attention is paid to the first window (having a size of XS×YS). Next, a procedure of arranging the windows to be explained below is repeated until all the windows are arranged.

Figure 8A:
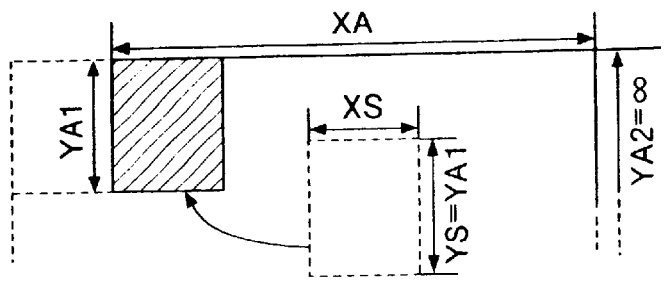
FIGS. 8A–8C show diagrams for explaining how to arrange the simulating windows.
Figure 8B:
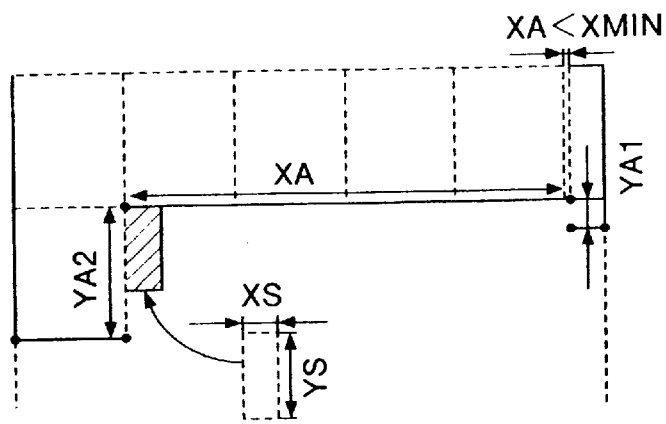
Figure 8C:
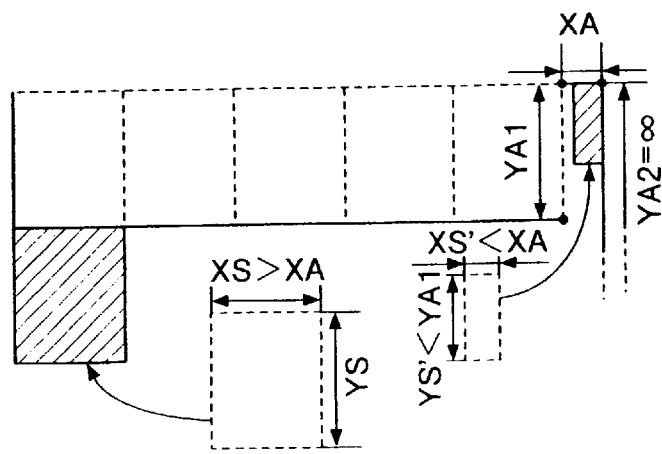

Attention is paid to one of the line segments having the minimum y coordinate value at a step 75, and a length XA of the attention-paid line segment, smaller one YA1 and larger one YA2 of differences in y coordinate value between the line segment in question and the line segments adjacent thereto are calculated and found at a step 76. The values YA1 and YA2 are considered to be infinite in the absence of the adjacent line segments and to be negative when the y coordinate value of the adjacent line segment is smaller. At a step 77, the value XA is first checked. When the value XA is less than Xmin and the values YA1 and YA2 are both positive as shown in FIG. 8C, the line segment in question is connected to the YA1-side line segment to form a single line segment at a step 78. At a step 79, attention is paid to the next smaller line segment with respect to the y coordinate value and control returns to the step 76.

Next, when XA≧Xmin at the step 77, the value XA is compared with the size XS of the window in the x direction at a step 80. When the value XA is larger than the value XS, the size YS of the window in the y direction is compared with the value YA1 at a step 81. When the value YS is equal to the value YA1 as shown in FIG. 8A, the window is arranged so that the line segment in question is contacted with the YA1-side line segment at a step 82. Otherwise, the window is arranged so that the line segment in question is contacted with the YA2-side line segment as shown in FIG. 8C at a step 83. As shown in FIG. 8B, when the value XA is smaller than the value XS at the step 80, one of the windows having an x-directional size of XA or less and y-directional size of YA1 or less (window having a size XS'×YS' smaller than YS×YA1) is searched. When such a window is found at a step 85, the found window is arranged at a step 86. When such a window fails to be found at the step 85, attention is paid to the next smaller line segment in the y coordinate value at a step 87, after which the similar operations are repeated until the arrangement of the window is completed.

When the x-directional size of the arranged window is equal to the value Xmin at a step 88, minimum one of the x-directional sizes of the remaining windows is set at Xmin at a step 89. The line segment data is updated and, at a step 90, attention is paid to the next window to arrange it in accordance with the similar procedure.

In this way, when the simulating windows are arranged, a rectangular region 54 containing all the windows can have a minimum size as shown in FIG. 6C, which means that the simulating image data 15 become minimum in size.

By the aforementioned image data collecting method, there can be generated the simulating image data 15 which is remarkably reduced in data capacity when compared with that of the detection image. For example, when the wired board structure 30 is employed, the simulating image data can be reduced by 10 to 20%. Accordingly, image data at many inspection points can be easily collected. Further, since the simulating window data 14 for specifying the image processing range, inspection contents, pat type, part number, pin number and lead direction are simultaneously or previously generated with respect to the simulating image data 15, easy defect judgement can be realized over the simulating image data 15.

Explanation will next be made as to the simulation of the image processor 4.

FIG. 9 shows a functional block arrangement of the image processor 4. The image processor 4 includes a feature extractor 41, a defect judger 42, an inspection window data designator 43, a detection image reconstructing part 44, an image processing parameter selector 45, a defect judgement parameter selector 46, a defect information storage 47 and an erroneous judgement/defect missing detector 48. The inspection window data designator 43 is used to designate the window data (inspection window data) according to the designation of the search key 60 or a predetermined input program. The image processing parameter selector 45 selects from the various image processing parameters 18 the image processing parameter 61 conforming to the inspection conditions (including the inspection contents, part type and lead direction) designated by designation 49 of parameters manually directly entered for parameter editing or designated by the inspection window data designator 43 of the inspection window data. The defect judgement parameter selector 46 also selects from the various defect judgement parameters 19 the defect judgement parameter 62 conforming to the inspection conditions (including the inspection contents, part type and lead direction) designated by designation 49 of parameters manually directly entered for parameter editing or designated by the inspection window data designator 43 of the inspection window data. The detection image reconstructing part 44 reconstructs the image data 15 stored in the memory device 6 into the detection image 68 of the image processing range indicated by the inspection windows on the basis of the lead address addr(i), data size size(i) and window width xe(i)−xs(i)+1 designated by the inspection window data designator 43. The feature extractor 41 extracts from the reconstructed detection image 68 structural feature parameters (such as, for example, a fillet height and length of a soldered part) of 2- or stereoscopic (3-dimensional) shape or physical properties on the basis of the above selected Image processing parameter 61. The defect judger 42 performs its defect judging operation over the extracted structural feature parameter 56 on the basis of the selected defect judgement parameter 62, and outputs its judgement result 20. And the judgement result 20 is displayed such a display means as a display provided to the image processor 4 or is output by an output means (including recording medium) provided to the image processor 4.

The defect information storage 47 inputs known defect data 67 that is known for or on a known inspection object to the known inspection window by means o f an input means, and stores the data as associated with the inspection window data 17 obtained from the inspection window data generator 13 or with the simulating window data 14 obtained from the window data generator 7. The erroneous judgement/defect missing detector 48 compares the judgement result 20 obtained as associated the inspection window data 17 from the known inspection window whose defect information is known for or on the inspection object with the known defect data stored as associated with the inspection window data 17 in the defect information storage 47 to detect erroneous judgement or defect missing. Its detected result is displayed on such a display means as a display provided to the image processor 4 or is output from an output means (including recording medium) provided to the image processor 4.

In the image processor 4, in a simulation mode, using the lead address addr(i), data size size(i) and window width xe(i)−xs(i)+1 of the simulation image designated by the inspection window data designator 43 on the basis of the window data; the detection image reconstructing part 44 reconstructs from the image data 15 the image of the image processing range indicated by the inspection window; the image processing parameter selector 45 selects the image processing parameter 61 corresponding to the reconstructed detection image on the basis of the various image processing parameters 18 under the inspection conditions (including detection contents, part type and lead direction) 59 designated by the inspection window data designator 43; the defect judgement parameter selector 46 selects the defect judgement parameter 62 corresponding to the reconstructed detection image from the various defect judgement parameters 19; the feature extractor 41 extracts the structural feature parameter 56 of 2-dimensional shape or stereoscopic shape (3-dimensional shape) or physical property from the selected image processing parameter 61 for the reconstructed detection image 68; and the defect judger 42 performs its defect judging operation over the extracted structural feature parameter 56 on the basis of the defect judgement parameter 62 and outputs the judgement result 20.

Further, the erroneous judgement or defect missing can be detected as associated with the inspection window data 17 by the erroneous judgement/defect missing detector 48. Therefore, the detected result can be used to change the selection of the image processing parameter corresponding to the inspection condition 59 based on the inspection window data designator 43 by the image processing parameter selector 45 according to the parameter designation 49 to realize optimization of the image processing parameter, and to change the selection of the defect judgement parameter corresponding to the inspection condition 59 based on the inspection window data designator 43 by the defect judgement parameter selector 46 to realize optimization of the defect judgement parameter. It goes without saying that the various image processing parameters 18 or various defect judgement parameters 19 may be modified according to the parameter designation 49. A result 63 detected by the erroneous judgement/defect missing detector 48 is applied as a parameter designation command 49 to the image processing parameter selector 45 and defect judgement parameter selector 46, so that the image processing parameter selector 45 selects the optimized image processing parameter from various image processing parameters and the defect judgement parameter selector 46 selects the optimized defect judgement parameter from the various defect judgement parameters.

As has been explained in the foregoing, since the generated window data 14 include data for specification of the image processing range for the simulating image data 15, the detection image reconstructing part 44 can easily reconstruct the detection image within the inspection window and the feature extractor 41 and defect judger 42 can easily realize defect judgement simulation over the reconstructed detection image 68 on the basis of the simulating window data 14 by applying the image processing operation thereto. Further, since the simulating window data 14 has the same information (part number, pin number, part type, etc.) as the inspection window data 17 as shown in FIG. 4, part of the items of the inspection window data 17 can be specified as the search key 60, the detection image reconstructing part 44 can selectively reconstruct the detection image, and the feature extractor 41 and defect judger 42 can perform their simulating operations. For example, when the part type is specified by the search key 60 to be 0.5 mm, the pitch is to be QFP and the inspection contents is to be soldered inspection; the inspection window data designator 43 searches the window data for the part type and inspection contents, selects only the window satisfying the inspection condition on the basis of the lead address addr(i), data size size(i) and window width xe(i)−xs(i)+1, the detection image reconstructing part 44 reconstructs the corresponding detection image, and the feature extractor 41 and defect judger 42 perform their simulating operations.

The present embodiment is the inspection apparatus which includes the image processor 4 for realizing a simulation function using the generated image data and window data, but only the image processor 4 for realizing the simulation function may be provided as separated therefrom.

Figure 10:
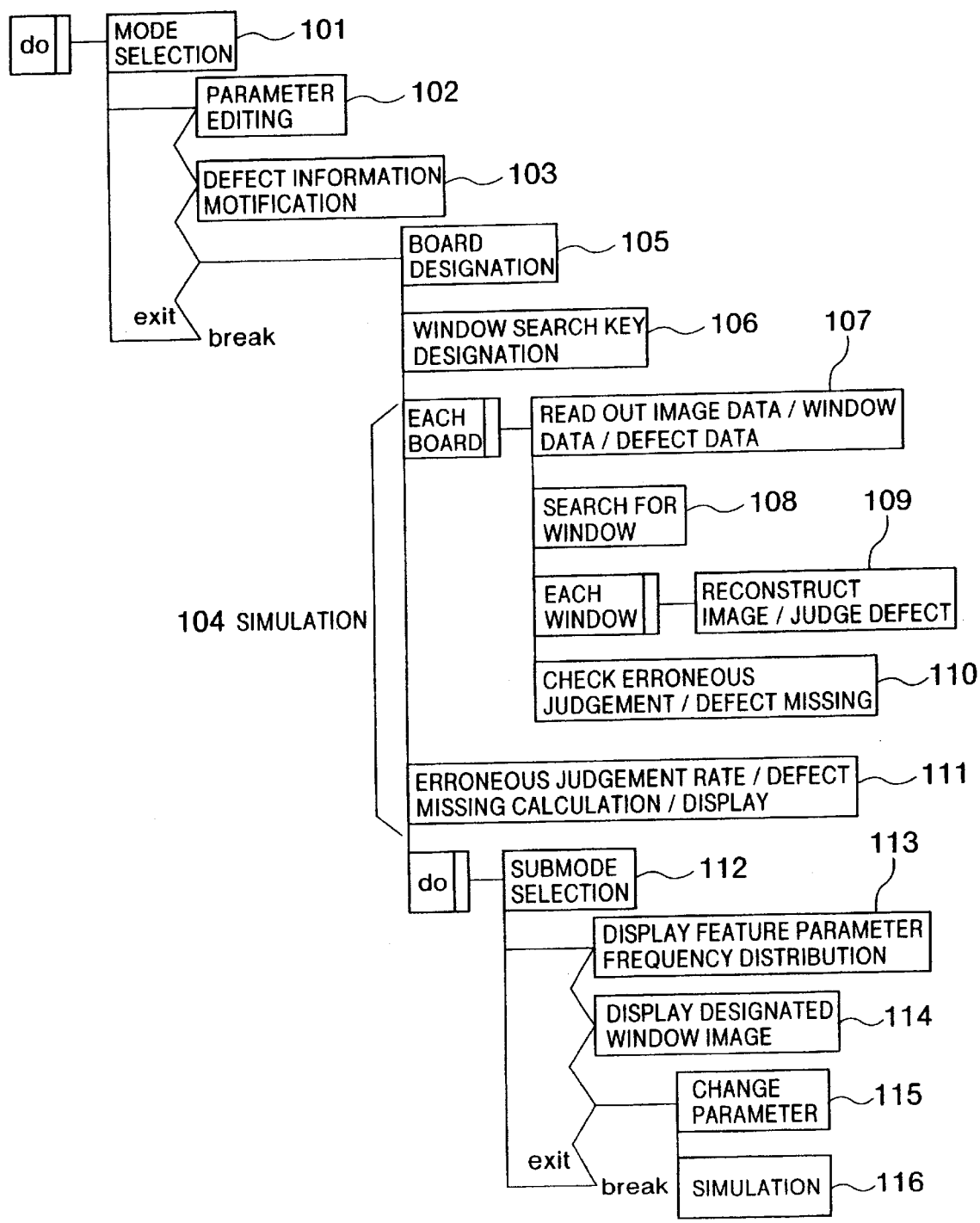
FIG. 10 is a flowchart for explaining an off line simulating program in the image processor of FIG. 9.

FIG. 10 shows an operational flowchart for realizing the simulation function of the present invention by the image processor 4 in an off line manner. At a mode selection step 101, an operator selects either one of modes of parameter editing 102, defect information notification (defect information input) 103 and simulation 104 with use of an input means to the CPU of the image processor 4.

When the operator selects the parameter editing mode 102 as the mode selection 101, the image processing parameter selector 45 selects the image processing parameter 61 selected from the various image processing parameters 18 according to the parameter designation 49, the defect judgement parameter selector 46 selects the defect judgement parameter 62 selected from the various defect judgement parameters 19 to thereby modify the image processing and defect judgement parameters. And through simulation to be explained later, the judgement result 20 corresponding to the modified image processing and defect judgement parameters can be output.

When the operator selects the defect information notification (defect information input) 103 as the mode selection 101, the operator specifies a board by its known board type and board number and enters the defect data 67 including part number/pin number and known defect type associated therewith with use of an input means, whereby the defect information storage 47 generates known defect data of a wired structure (inspection object) for the specified board. The defect data is used, in the simulation mode, to cause the erroneous judgement/defect missing detector 48 to check erroneous judgement that a normal product is judged as defective or defect missing that a defective product is judged as good.

When the operator selects the simulation 104 as the mode selection 101, the operator specifies a wired board by its board type and board number at a step 105. At a next step 106, the operator specifies part of the items of the simulating window data 14 as the search key 60. These specifications can be made each in plural numbers, and also can be all made by the inspection window data designator 43 of the inspection window data. At a next step 107, the simulating image data 15 and simulating window data 14 for each of the specified boards are read out from the memory device 6 and the defective data for each specified board is read out from the defect information storage 47.

The inspection window data designator 43 searches for the simulating window data 14 with use of the specified search key 60 at a step 108. At a step 109, with respect to the searched window, the detection image reconstructing part 44 reconstructs the detection image with use of the specified window data 58 from the image data 15; the feature extractor 41 extracts the structural feature parameter 56 corresponding to the modified image processing parameter from the reconstructed detection image; and the defect judger 42 performs its defect judging operation over the extracted structural feature parameter 56 according to the modified defect judgement parameter. At a step 110, next, the erroneous judgement/defect missing detector 48 compares the defect judgement result 20 issued from the defect judger 42 with defect data 57 read out from the defect information storage 47 to detect erroneous judgement and defect missing and also to display them on the display means. At the steps 107 to 110, with respect to all the specified boards, defect judgement is carried out to detect the erroneous judgement and defect missing. At a step 111, the erroneous judgement/defect missing detector 48 calculates a percentage of frequency of erroneous judgement to the number of all good products (i.e., erroneous judgement ratio) as well as a percentage of frequency of defect missing to the total good product number (i.e., defect missing ratio) 63 to display them on the display means.

At a next step 112, the operator selects one of submodes of graph display, image display and parameter modification with use of the input means to the CPU of the image processor 4. Selection of the graph display causes a frequency distribution 65 of the structural feature parameter obtained from the feature extractor 41 in the specified item based on the search key 60 to be found and displayed on the display means in the form of a graph at a step 113. Selection of the image display causes the detection image 66 corresponding to the window determined by the specified part number and pin number to be obtained from the detection image reconstructing part 44 with use of the search key 60 and to be displayed on the display means at a step 114. Selection of the parameter modification causes the parameter to be modified as in the above parameter editing mode according to the parameter designation 49 at a step 115, after which at a step 116, the feature extractor 41 and defect judger 42 again perform their simulating operations with use of the modified parameter. The above operations can be repetitively selected and executed by the image processor 4. Thus, while the operator monitors the erroneous judgement ratio, defect missing rate 63 and structural feature parameter frequency distribution 65 displayed on the display means, the operator can slightly modify the parameter according to the parameter designation 49 to repeat the simulation, thereby enabling the optimization of the image processing and defect judgement parameters. These parameters can be used in the aforementioned visual inspection apparatus.

As has been explained above, the image processor 4 can optimize parameters for use in inspection without any break in the inspection.

Even when the operator wants to leave the inspection history, he can record or store in a disk or the like the judgement result 64, erroneous judgement ratio and defect missing ratio 63 obtained by specifying a minimum number of necessary windows based on the designation of the search key 60.

In accordance with the present invention, only data of a range indicated by each inspection window data is cut out from the detection image to form image data, so that missing of information necessary for the defect judgment can be avoided, the data capacity can be remarkably reduced when compared with that of the detection image, a write time to the image memory device can be shortened, and window data for specifying an image processing range for each inspection window can be generated. As a result, the input of the image data and window data advantageously enables easy implementation of the defect judging simulation based on the image processing equivalent to the inspection. That is, by generating simulation data for many inspection points and repeating the defect judgement simulation while changing the parameters, the parameters can advantageously be easily optimized.

Further, the present invention can advantageously exhibit of an effect of realizing the reliable defect judgement without any erroneous judgement or defect missing while optimizing the image processing and defect judgement parameters for the detection image cut out by each inspection window.

Furthermore, when it is desired to perform reliable defect judgement over the detection image cut out by each inspection window, the present invention can realize such simulation as to optimize the image processing and defect judgement parameters without any erroneous judgement or defect missing.

What is claimed is:

1. A defect judgement processing method comprising the steps of:

detecting by image detection means an image of an object to be inspected;

cutting out by image data generator means ranges indicated by a plurality of predesignated inspection windows from the detected image and storing the ranges in memory means;

generating by window data generator means window data having an inspection condition attached thereto for each of said plurality of inspection windows and storing the window data in said memory means;

reading out by a feature extractor the window data corresponding to the respective inspection windows stored in said memory means;

selecting an image processing parameter conforming to the inspection condition obtained by each window data and further extracting a structural feature parameter from the detection image of the range indicated by each inspection window read out from said memory means on the basis of said selected image processing parameter;

selecting by a defect judger a defect judgement parameter conforming to said inspection condition; and performing its defect judging operation over the extracted structural feature parameter on the basis of said selected defect judgement parameter.

2. A defect judgement processing method comprising the steps of:

detecting by image detection means an image of an object to be inspected, cutting out by image data generator means ranges indicated by a plurality of predesignated inspection windows from the detected image and storing the ranges in memory means;

generating by window data generator means window data having an inspection condition attached thereto for each of said plurality of inspection windows and storing the window data in said memory means;

reading out a feature extractor the detection image of the range indicated by each inspection window from said memory means;

reading out the window data corresponding to the respective inspection windows stored in said memory means and extracting a structural feature parameter therefrom on the basis of an image processing parameter conforming to the inspection condition obtained by each window data;

performing by a defect judger its defect judging operation over the extracted structural feature parameter on the basis of a defect judgement parameter conforming to said inspection condition; and comparing its defect judgement with defect information previously stored as associated with said each inspection window to detect erroneous judgement or defect missing.

3. A defect judgement processing method comprising the steps of:

detecting by image detection means an image of an object to be inspected;

cutting out by image data generator means ranges indicated by a plurality of predesignated inspection windows from the detected image and storing the ranges in memory means;

generating by window data generator means window data having an inspection condition attached thereto for each of said plurality of inspection windows and storing the window data in said memory means;

reading out by a feature extractor the detection image of the range indicated by each inspection window from said memory means;

reading out the window data corresponding to the respective inspection windows stored in said memory means and extracting a structural feature parameter therefrom on the basis of an image processing parameter selected according to the inspection condition obtained by each window data;

performing by a defect judger its defect judging operation over the extracted structural feature parameter on the basis of a defect judgement parameter selected according to said inspection condition;

comparing its defect judgement with defect information previously stored as associated with said each inspection window to detect erroneous judgement or defect missing; and optimizing said selected image processing parameter or defect judgement parameter according to the detected erroneous judgement or defect missing.

4. A defect judgement processing method comprising the steps of:

detecting by image detection means an image of an object to be inspected;

cutting out by image data generator means ranges indicated by a plurality of predesignated inspection windows from the detected image and storing the ranges in memory means;

generating by window data generator means window data having an inspection condition attached thereto for each of said plurality of inspection windows and storing the window data in said memory means;

reading out by a feature extractor the detection image of the range indicated by each inspection window from said memory means;

reading out the window data corresponding to the respective inspection windows stored in said memory means and extracting a structural feature parameter therefrom on the basis of an image processing parameter conforming to the inspection condition obtained by each window data;

performing by a defect judger its defect judging operation over the extracted structural feature parameter on the basis of a defect judgement parameter conforming to said inspection condition; and comparing its defect judgement with defect information previously stored as associated with said each inspection window to detect erroneous judgement or defect missing and to display it on display means.

5. A defect judgement processing method comprising the steps of:

detecting by image detection means an image of an object to be inspected;

cutting out by image data generator means ranges indicated by a plurality of predesignated inspection windows from the detected image and storing the ranges in memory means;

generating by window data generator means window data having an inspection condition attached thereto for each of said plurality of inspection windows and storing the window data in said memory means;

reading out by a feature extractor the detection image of the range indicated by each inspection window from said memory means;

reading out the window data corresponding to the respective inspection windows stored in said memory means and extracting a structural feature parameter therefrom on the basis of an image processing parameter conforming to the inspection condition obtained by each window data;

performing by a defect judger its defect judging operation over the extracted structural feature parameter on the basis of a defect judgement parameter conforming to said inspection condition;

displaying its defect judgement on display means; and comparing its defect judgement with defect information previously stored as associated with said each inspection window to detect erroneous judgement or defect missing and to display it on the display means.

6. A defect judgement processing method comprising the steps of:

detecting by image detection means an image of an object to be inspected;

cutting out by image data generator means ranges indicated by a plurality of predesignated inspection windows from the detected image and storing the ranges in memory means;

generating by window data generator means window data having an inspection condition attached thereto for each of said plurality of inspection windows and storing the window data in said memory means;

reading out by a feature extractor the detection image of the range indicated by each inspection window from said memory means;

reading out the window data corresponding to the respective inspection windows stored in said memory means and extracting a structural feature parameter therefrom on the basis of an image processing parameter conforming to the inspection condition obtained by each window data;

performing by a defect judger its defect judging operation over the extracted structural feature parameter on the basis of a defect judgement parameter conforming to said inspection condition;

displaying said extracted structural feature parameter on display means; and comparing its defect judgement with defect information previously stored as associated with said each inspection window to detect erroneous judgement or defect missing and to display it on the display means.

7. A defect judgement processing method for applying an image processing operation to perform defect judgement, comprising the steps of:

specifying as a search key part of items of inspection window data including data for specifying an image processing range and an inspection condition;

selecting the inspection window data on the basis of the specified search key; and cutting out only the data of a detection image of the range indicated by the selected inspection window data to collect image data and store it.

8. A defect judgement processing apparatus comprising:

image detection means for detecting an image of an object to be inspected;

memory means;

image data generator means for cutting out ranges indicated by a plurality of predesignated inspection windows from the detected image and for storing the ranges in said memory means;

window data generator means for generating window data having an inspection condition attached thereto for each of said plurality of inspection windows and for storing the window data in said memory means;

feature extraction means for reading out the detection image of the range indicated by each inspection window from said memory means, for reading out the window data corresponding to the respective inspection windows stored in said memory means and for extracting a structural feature parameter therefrom on the basis of an image processing parameter conforming to the inspection condition obtained by each window data; and defect judgement means for performing its defect judging operation over the extracted structural feature parameter on the basis of a defect judgement parameter conforming to said inspection condition.

9. A defect judgement processing apparatus comprising:

image detection means for detecting an image of an object to be inspected;

memory means;

image data generator means for cutting out ranges indicated by a plurality of predesignated inspection windows from the detected image and for storing the ranges in said memory means;

window data generator means for generating window data having an inspection condition attached thereto for each of said plurality of inspection windows and for storing the window data in said memory means;

feature extraction means for reading out the detection image of the range indicated by each inspection window from said memory means, for reading out the window data corresponding to the respective inspection windows stored in said memory means and for extracting a structural feature parameter therefrom on the basis of an image processing parameter conforming to the inspection condition obtained by each window data;

defect judgement means for performing its defect judging operation over the extracted structural feature parameter on the basis of a defect judgement parameter conforming to said inspection condition; and detection means for comparing a defect judgement result obtained by said defect judgement means with defect information previously stored as associated with said each inspection window to detect erroneous judgement or defect missing.

10. A defect inspection method comprising the steps of:

obtaining an image of a sample;

storing an image selected from said obtained image;

extracting an image which fits a desired reference condition from said stored image;

obtaining information relating to a defect by processing said extracted image using a parameter for inspection which includes at least an image processing parameter and a defect judgement parameter; and outputting information relating to at least one of an erroneous judgement ratio and a defect missing ratio in accordance with said parameter for inspection from said obtained information.

11. A defect inspection method according to claim 10, wherein said desired reference condition is inputted from an external device.

12. A defect inspection method according to claim 10, further comprising a step for displaying on a screen of a display device the at least one of the erroneous judgement ratio and the defect missing ratio.

13. A defect inspection method comprising the steps of:

obtaining an image of a sample;

processing an image selected from said obtained image using a predetermined processing condition and obtaining information relating to at least one of an erroneous judgement ratio and a defect missing ratio;

correcting said predetermined processing condition on the basis of said information relating to the at least one of the erroneous judgement ratio and the defect missing ratio; and inspecting a defect of the sample using said corrected processing condition.

14. A defect inspection method according to claim 13, further comprising a step of obtaining said information relating to the at least one of the erroneous judgement ratio and the defect missing ratio on the basis of an inspection result of the defect of the sample in accordance with said corrected processing condition.

15. A defect inspection method according to claim 13, wherein said predetermined processing condition includes an image processing parameter and a defect judgement parameter.

16. A defect inspection method according to claim 13, further comprising a step of displaying at least one of the erroneous judgement ratio and the defect missing ratio on a display.

17. A defect inspection method comprising steps of:

obtaining an image of said sample;

storing an image selected from said obtained image;

processing said stored image using a predetermined processing condition to execute a simulation for a defect judgement;

correcting said predetermined processing condition on the basis of a result of the simulation; and inspecting a defect of the sample using said corrected processing condition.

18. A defect inspection method according to claim 17, wherein said predetermined processing condition includes an image processing parameter and a defect judgement parameter.

19. A defect inspection method according to claim 17, wherein said stored image is an image data and in the step of processing said image data is restored to an image and the restored image is Processed using said predetermined processing condition to execute a simulation of the defect judgement.

20. A defect inspection apparatus comprising:

image obtaining means for obtaining an image of sample;

storing means for storing an image selected from said image obtained by said image obtaining means;

image extracting means for extracting an image which fits to a desired reference condition from said stored image;

information obtaining means for obtaining information relating to a defect by processing said image extracted by said image extracting means by using a parameter for inspection which includes at least an image processing parameter and a defect judgement parameter; and calculating means for calculating at least one of an erroneous judgement ratio and a defect missing ratio by using said parameter for inspection based on said information relating to the defect obtained by said information obtaining means and outputting a result of the calculating.

21. A defect inspection apparatus according to claim 20, wherein said calculating means includes a display unit and wherein said information relating to at least one of the erroneous judgement ratio and the defect missing ratio is displayed on a screen of said display unit.

22. A defect inspection apparatus comprising:

image obtaining means which obtains an image of said sample;

calculation means for selecting a partial image of said image obtained by said image obtaining means and processing said selected partial image on the basis of a predetermined processing condition to obtain information relating to at least one of an erroneous judgement ratio and a defect missing ratio;

correcting means for correcting said predetermined processing condition using at least one of the erroneous judgement ratio and the defect missing ratio obtained by said calculation means; and inspection means for inspecting a defect of the sample in accordance with the predetermined processing condition corrected by said correcting means.

23. A defect inspection apparatus according to claim 22, wherein said calculation means further obtains information relating to the at least one of the erroneous judgement ratio and the defect missing ratio on the basis of a result obtained by inspecting the defect of the sample by using the predetermined processing condition corrected by said correcting means.

24. A defect inspection apparatus according to claim 22, wherein said predetermined processing condition includes an image processing parameter and defect judgement parameter.

25. A defect inspection apparatus according to claim 22, wherein said calculating means includes a display unit and wherein said information relating to the at least one of the erroneous judgement ratio and the defect missing ratio is displayed on a screen of said display unit.

26. A defect inspection apparatus comprising:

image obtaining means which obtains an image of a sample;

storing means which stores an image of said image obtained by said image obtaining means;

simulation means which processes an image stored in said storing means by using a predetermined processing condition to execute a simulation for a defect judgement;

correcting means which corrects said predetermined processing condition using a simulation result executed by said simulation means; and inspection means for inspecting a defect of the sample by using said processing condition corrected by said correcting means.

27. A defect inspection apparatus according to claim 26, wherein said predetermined processing condition includes an image processing parameter and a defect judgement parameter.

28. A defect inspection apparatus according to claim 26, wherein said storing means stores said image as image data and said simulation means processes an image obtained by restoring said stored image data on the basis of said predetermined processing condition to execute the simulation of the defect judgement.

* * * * *